United States Patent [19] [11] Patent Number: 5,865,727
Sano et al. [45] Date of Patent: Feb. 2, 1999

[54] PORTABLE ENDOSCOPE SYSTEM

[75] Inventors: Hiroshi Sano; Rensuke Adachi; Hirohisa Ueda; Kunitoshi Ikeda; Kunikiyo Kaneko; Takashi Koeda, all of Tokyo, Japan

[73] Assignee: Asahi Kogaku Kogyo Kabushiki Kaisha, Tokyo, Japan

[21] Appl. No.: 696,179

[22] Filed: Aug. 13, 1996

[30] Foreign Application Priority Data

Aug. 25, 1995 [JP] Japan ................................. 7-216837
Mar. 9, 1996 [JP] Japan ................................. 8-049967

[51] Int. Cl.⁶ ...................................................... A61B 1/06
[52] U.S. Cl. ........................... 600/178; 600/160; 600/101; 600/134; 600/131
[58] Field of Search ..................................... 600/131, 101, 600/134, 160, 178, 179, 180, 181, 182, 199, 248, 249, 197, 245

[56] References Cited

U.S. PATENT DOCUMENTS

| 2,235,979 | 3/1941 | Brown ..................................... 600/178 |
| 4,561,430 | 12/1985 | Walsh ..................................... 600/178 |
| 4,580,198 | 4/1986 | Zinnanti, Jr. ........................... 600/178 X |
| 4,823,244 | 4/1989 | Alaybayoglu et al. ................. 600/178 X |
| 5,588,950 | 12/1996 | Sano et al. ............................... 600/178 |

Primary Examiner—Beverly M. Flanagan
Attorney, Agent, or Firm—Greenblum & Bernstein, P.L.C.

[57] ABSTRACT

A portable endoscope having a control part containing an entrance end portion of a light guide for transmitting light for illuminating an object, and a hermetic illuminating light supply unit containing a light source lamp for supplying illuminating light to the light guide. The unit is connected to the control part. An armoring member is disposed at a position where it is heated by heat radiated from the light source lamp. The outer surface of the armoring member is covered with a heat-insulating cover made of a material having a low thermal conductivity. A battery chamber is formed in the illuminating light supply unit to accommodate a battery as a power supply for the lamp. A relief valve releases the pressure in the battery chamber to the outside of the unit when the pressure rises.

3 Claims, 8 Drawing Sheets

PORTABLE ENDOSCOPE SYSTEM

BACKGROUND OF THE INVENTION

1. Field of the Invention

The present invention relates to subject matter contained in Japanese Patent Application No. 7-216837 (filed on Aug. 25, 1995) and Japanese Patent Application No. 8-49967 (filed on Mar. 7, 1996), which are expressly incorporated herein by reference in their entireties.

The present invention relates to a portable endoscope in which a unit for supplying illuminating light to a light guide is attached to an endoscope control part.

2. Description of the Prior Art

A conventional portable endoscope has a light-emitting device for illumination which is provided in an endoscope control part. Such a conventional portable endoscope is generally arranged such that an entrance end portion of a light guide for transmitting light for illuminating an object is disposed in the endoscope control part, and an illuminating light supply unit is attached to the control part. The illuminating light supply unit contains a light source lamp for supplying illuminating light to the light guide and a power supply for the lamp, e.g. a dry battery.

Many of such conventional portable endoscopes adopt a structure in which the illuminating light supply unit is adapted to be detachable with respect to the endoscope control part, and a connecting cylinder for connecting the illuminating light supply unit projects from the control part.

Consequently, the connecting cylinder is heated by heat radiated from the light source lamp disposed in the distal end portion of the illuminating light supply unit, and this may cause the operator to feel uncomfortable when touching the heated connecting cylinder. Thus, the heated connecting cylinder may interfere with an endoscopic operation.

In many cases, the illuminating light supply unit of such a portable endoscope is formed into a hermetic structure from the necessity of washing, disinfection, etc.

However, if a gas is generated from the battery on account of some trouble occurring in the battery due to inappropriate management, the gas pressure in the illuminating light supply unit rises abnormally, giving rise to problems: a weak portion of the outer wall may be broken; and a cap and associated members which are removed from the unit on lamp replacement or battery replacement may be blown away by the high pressure in the unit at the instant of being disengaged from the unit.

SUMMARY OF THE INVENTION

An object of the present invention is to provide a portable endoscope which is designed so that an endoscopic operation is not hindered by heat radiated from a light source lamp contained in an illuminating light supply unit.

Another object of the present invention is to provide a light source apparatus for an endoscope, which is designed so that the pressure in a hermetic illuminating light supply unit will not abnormally rise even if a gas is generated from a battery accommodated in the unit.

Other objects and advantages of the present invention will become apparent from the following detailed description of illustrated embodiments of the invention.

According to the present invention, there is provided a portable endoscope having a control part containing an entrance end portion of a light guide for transmitting light for illuminating an object, and an illuminating light supply unit containing a light source lamp for supplying illuminating light to the light guide. The illuminating light supply unit is connected to the control part. The portable endoscope includes an armoring member disposed at a position where it is heated by heat radiated from the light source lamp, and a heat-insulating cover covering the outer surface of the armoring member. The heat-insulating cover is made of a material having a low thermal conductivity.

In addition, there is provided a portable endoscope having a control part containing an entrance end portion of a light guide for transmitting light for illuminating an object, and a hermetic illuminating light supply unit containing a light source lamp for supplying illuminating light to the light guide. The illuminating light supply unit is connected to the control part. The portable endoscope includes a battery chamber formed in the illuminating light supply unit to accommodate a battery as a power supply for lighting the light source lamp, and a relief valve for releasing the pressure in the battery chamber to the outside of the illuminating light supply unit when the pressure rises.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

FIGS. 1 to 5 show a first embodiment of the present invention.

Figure 1:
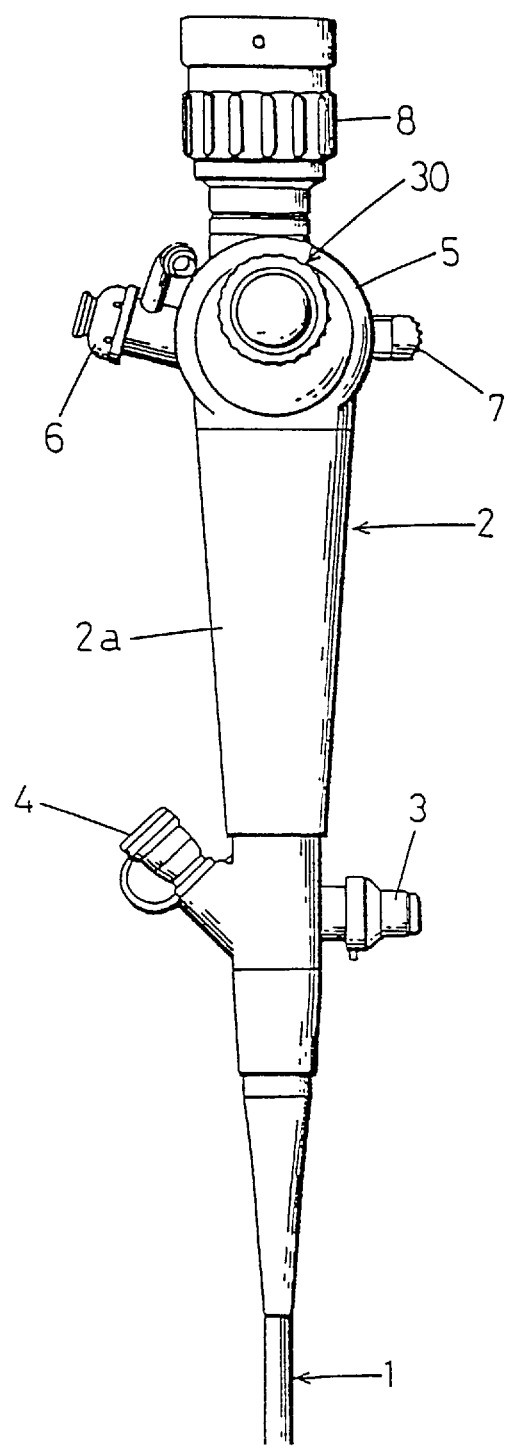
FIG. 1 is a side view of a portable endoscope according to a first embodiment of the present invention.
Figure 2:
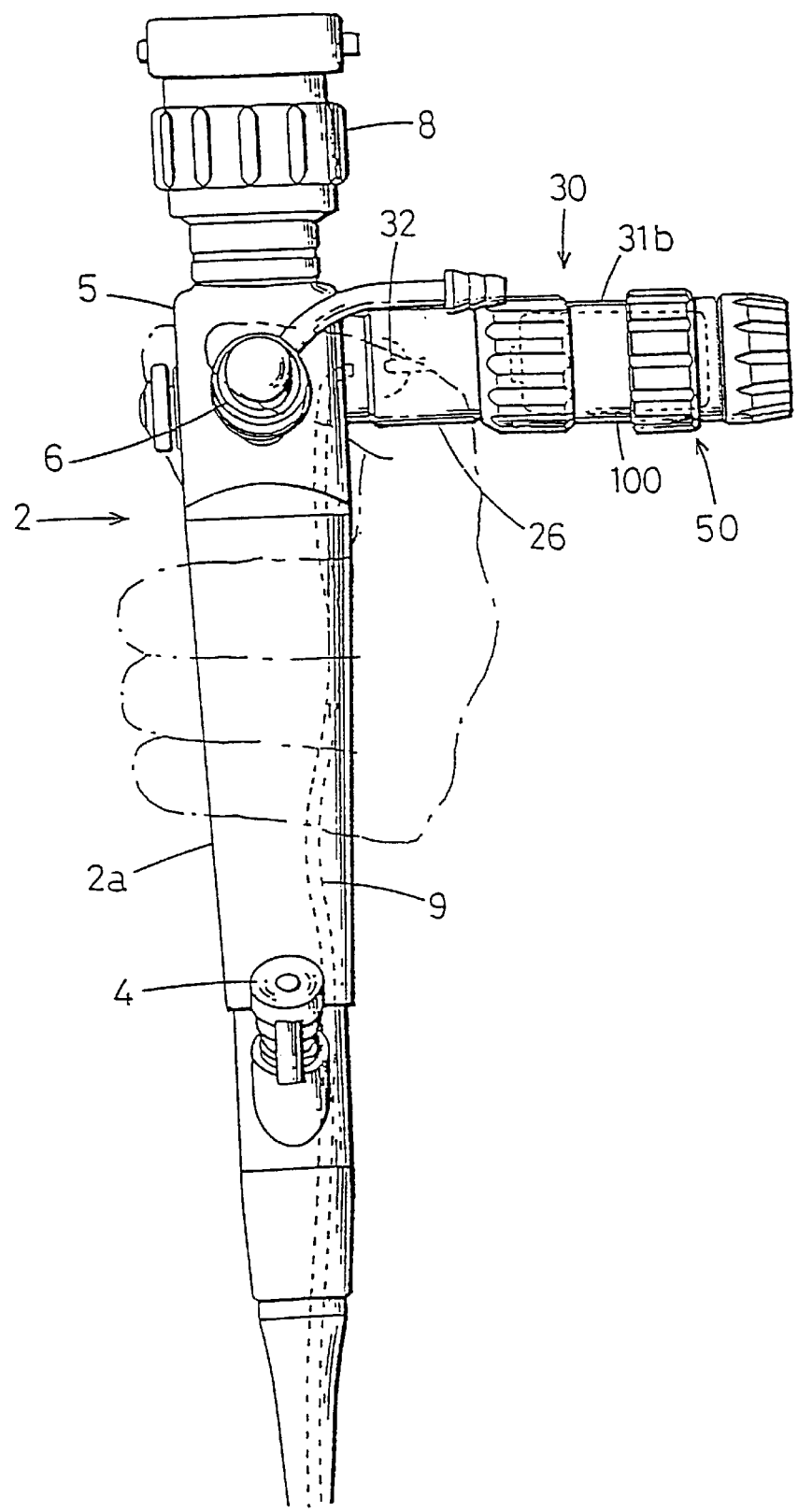
FIG. 2 is a front view of the portable endoscope according to the first embodiment of the present invention.

FIG. 1 is a side view of a portable endoscope according to the first embodiment of the present invention, particularly showing a control part 2 of the endoscope. FIG. 2 is a front view of the portable endoscope. The portable endoscope has an insert part 1 which is armored with a flexible tube. The proximal end of the insert part 1 is connected to the lower end portion of the control part 2.

About three fourths from the bottom of the control part 2 is a grip portion 2a. A forceps inlet 4 is provided between the grip portion 2a and the insert part 1 so as to project obliquely forward. A pressure control valve 3 is used to control the pressure in the endoscope, which is formed into a hermetic structure.

The control part 2 has a control mechanism portion 5 above the grip portion 2a. The control mechanism portion 5 has a suction control valve 6 which is disposed on the front side thereof to carry out a suction operation through a forceps channel (not shown) inserted in the insert part 1. The control mechanism portion 5 further has a bending control lever 7 which is disposed on the rear side thereof to effect bending control of a remote-controlled bendable portion (not shown) which is formed at the distal end of the insert part 1. In addition, an eyepiece 8 is provided on the top of the control mechanism portion 5.

A light guide fiber bundle 9 for transmitting light for illuminating an object has an entrance end portion disposed in the control mechanism portion 5, and extends through the insert part 1 and the grip portion 2a of the control part 2. The exit end portion of the light guide fiber bundle 9 is disposed in the distal end of the insert part 1.

An illuminating light supply unit 30 for supplying illuminating light to the light guide fiber bundle 9 is detachably connected to a side of the control mechanism portion 5.

As shown in FIG. 2, the illuminating light supply unit 30 contains a light source lamp 32 that emits illuminating light which is to be supplied to the light guide fiber bundle 9, and a battery 100 or the like which serves as a power supply for lighting the light source lamp 32. The battery 100 may be any type of battery, e.g. a dry battery or a rechargeable nickel-cadmium battery.

The battery 100 can be replaced by removing a cap 50 which is detachably attached to the outer end of the illuminating light supply unit 30. An AC/DC adapter or the like may be connected to the illuminating light supply unit 30 in place of the battery 100.

Figure 3:
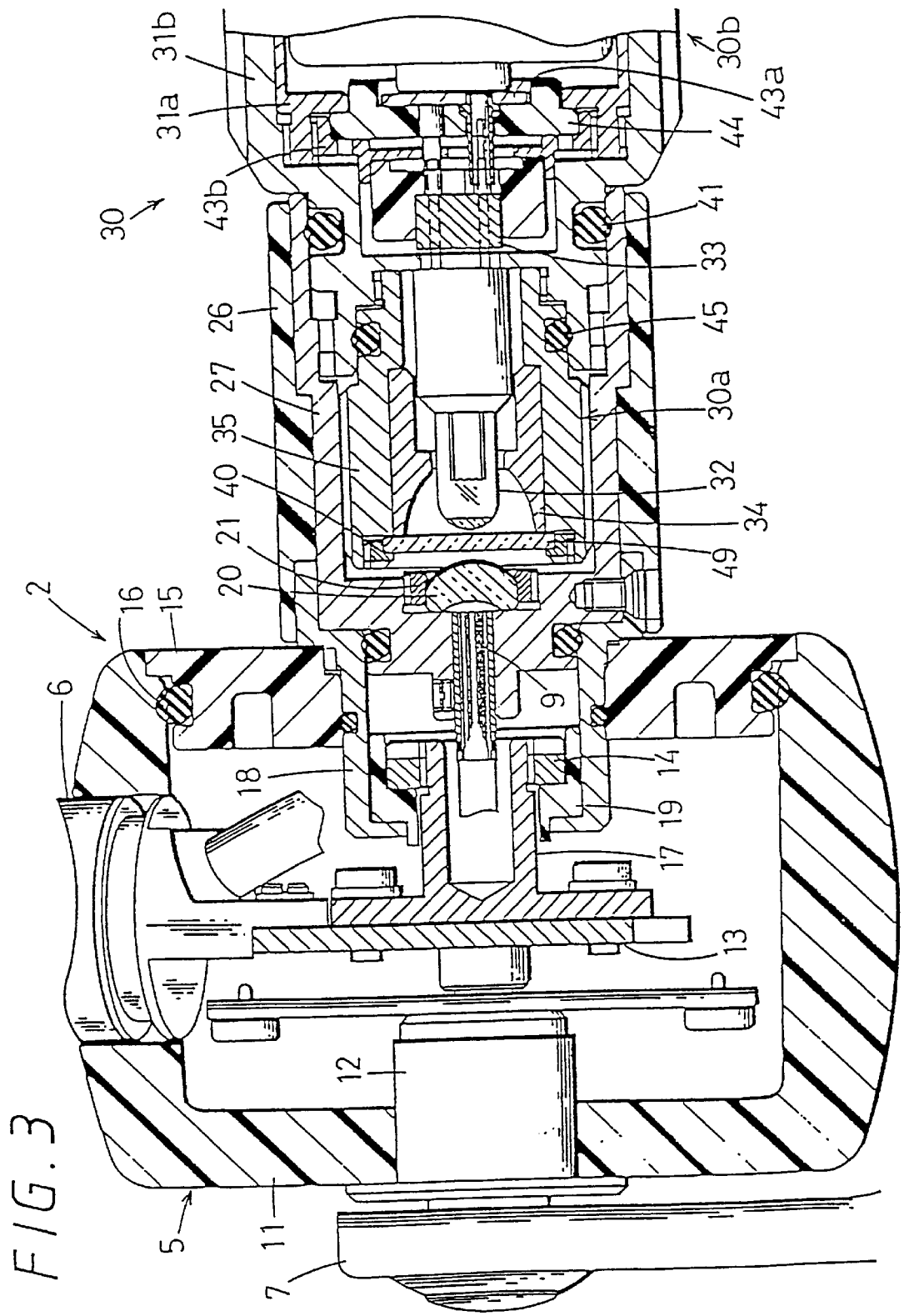
FIG. 3 is a fragmentary sectional view of the first embodiment of the present invention, showing a joint between an endoscope control part and an iiluminating light supply unit.

FIG. 3 shows a joint between the control part 2 and the illuminating light supply unit 30. The control mechanism portion 5 of the control part 2 is armored with a casing 11 made of an electrically insulating plastic material.

A lever bearing cylinder 12 that supports the bending control lever 7 is fitted in a hole provided in the casing 11, and sealed in a watertight manner. Similarly, the suction control valve 6 is fitted in a hole provided in the casing 11, and sealed in a watertight manner. The respective proximal end portions of the lever bearing cylinder 12 and the suction control valve 6 are secured to a metallic frame 13 in the control part 2.

A cover 15, which is made of an electrically insulating plastic material, is fitted in a relatively large opening provided in a side of the casing 11, and a sealing O-ring 16 is attached to the fitting surface of the cover 15 to prevent water from entering the inside of the control part 2 through the gap between the cover 15 and the peripheral wall of the opening.

Further, a detent (not shown) is formed in the area of fit between the cover 15 and the casing 11 to prevent the two members from rotating relative to each other. It should be noted that, although the O-ring 16 is compressed when it is disposed in the area of fit between the cover 15 and the casing 11, the cross-section of the O-ring 16 in a natural state before it is compressed is shown in the figure (the same shall apply hereinafter).

A support cylinder 17 is disposed on the central axis of a through-hole formed in the center of the cover 15. The proximal end portion of the support cylinder 17 is secured to the frame 13 in the control part 2. A connecting socket retainer 18 is secured to the cover 15 by being pressed with a fastening ring 14 which is thread-engaged with the head portion of the support cylinder 17. An insulating cylinder 19, which is made of an electrically insulating plastic material, is interposed between the connecting socket retainer 18 and the fastening ring 14 to prevent these members from coming in contact with each other.

The connecting socket retainer 18 opens to a considerable extent on the outer surface of the cover 15. The proximal end portion of a unit connecting socket 27 is screwed to the open end portion of the connecting socket retainer 18. The unit connecting socket 27 is formed, for example, of a stainless steel in the shape of a cylinder projecting outwardly from the control part 2 to connect the illuminating light supply unit 30.

A cylindrical cover (heat-insulating cover) 26 is provided to cover all the outer peripheral surfaces of the unit connecting socket 27 and the connecting socket retainer 18. The cylindrical cover 26 is made of a synthetic resin material having a low thermal conductivity. The cylindrical cover 26 has a projection formed on the inner surface thereof. With the projection held between the unit connecting socket 27 and the connecting socket retainer 18, the cylindrical cover 26 is immovably secured.

The entrance end portion of the light guide fiber bundle 9 is secured with a screw at the central axis position in the bottom of the unit connecting socket 27. A convex meniscus lens 20 is secured so as to face the entrance end surface of the light guide fiber bundle 9 by a retaining nut 21 which is thread-engaged with a bottom surface portion of the unit connecting socket 27.

It should be noted that a sealing O-ring is disposed in the area of fit between each pair of mating members disposed inside the bore of the cover 15, thereby forming the control part 2 into a watertight structure which prevents water from externally entering the control part 2 through any portion thereof. The insert part 1 is similarly formed into a watertight structure, as a matter of course.

The illuminating light supply unit 30 has a straight cylindrical configuration as a whole. The illuminating light supply unit 30 is divided into a lamp chamber portion 30a, which is closer to the joint to the control part 2, and a battery chamber portion 30b, which is away from the joint to the control part 2. FIG. 3 shows the whole lamp chamber portion 30a.

The outer wall of the battery chamber portion 30b is formed by an outer casing 31b which is made of a material of good corrosion resistance (chemical resistance), for example, a stainless steel, a metallic material which has been subjected to chemical-resistant surface treatment, or a plastic material. Further, a cylindrical inner casing 31a is disposed inside the outer casing 31b in contact with the inner peripheral surface of the outer casing 31b. The inner casing 31a is made of a material of good electrical conductivity, for example, copper, or a copper alloy such as phosphor bronze.

A lamp socket 33 is secured to the inner casing 31a through some parts at the boundary between the lamp chamber portion 30a and the battery chamber portion 30b. The light source lamp 32 is detachably inserted into the lamp socket 33. The lamp socket securing structure will be described later.

A cylindrical lamp chamber casing 35 forms the outer wall of the lamp chamber portion 30a. The lamp chamber casing 35 is formed of a material of mechanical strength, for example, a stainless steel, and connected to the outer casing 31b by thread engagement.

Accordingly, when the lamp chamber casing 35 is disengaged from the outer casing 31b, the light source lamp 32, which is disposed in the lamp chamber casing 35, is exposed. Thus, the light source lamp 32 can be replaced. An O-ring 45 seals the area of joint between the lamp chamber casing 35 and the outer casing 31b.

A reflecting mirror 34 is secured in the distal end portion of the lamp chamber casing 35 so as to surround the light source lamp 32 in order to converge illuminating light from the light source lamp 32 toward the entrance end surface of the light guide fiber bundle 9.

A transparent cover glass 49 is secured to the front end surface of the reflecting mirror 34 by a retaining nut 40. The outer peripheral surface of the cover glass 49 is coated with a sealing compound to prevent water from externally entering the lamp chamber casing 35.

An external thread is formed on the outer peripheral surface of the distal end portion of the outer casing 31b. The external thread is engageable with an internal thread which is formed on the inner peripheral surface of the intermediate portion of the unit connecting socket 27. By engaging the two threads with each other, the illuminating light supply unit 30 is connected to the control part 2.

Consequently, illuminating light that is emitted from the light source lamp 32 is reflected by the reflecting mirror 34, and then passes through the cover glass 49 and the convex meniscus lens 20. Thus, the illuminating light converges on the entrance end surface of the light guide fiber bundle 9, and enters the light guide fiber bundle 9.

At this time, metallic armoring parts, such as the unit connecting socket 27 and the connecting socket retainer 18 contiguous to it, are heated by heat radiated from the light source lamp 32. However, the outer peripheral surfaces of these parts are entirely covered with the cylindrical cover 26 of low thermal conductivity. Therefore, as shown in FIG. 2, the operator's hand gripping the control part 2 touches only the surface of the cylindrical cover 26, and does not feel the heat.

It should be noted that heat radiated from the light source lamp 32 is further transferred from the unit connecting socket 27 to the outer casing 31b and dissipates from the outer surface of the illuminating light supply unit 30. However, because the outer casing 31b is away from the part that is directly heated by the light source lamp 32, the rise in the temperature of the outer casing 31b is small. In addition, it is unlikely that the operator's hand will touch the illuminating light supply unit 30 because it is away from the control part 2.

The illuminating light supply unit 30 is detached from the control part 2 by disengaging the outer casing 31b from the unit connecting socket 27. An O-ring 41 seals the area of fit between the lamp chamber casing 35 and the unit connecting socket 27 when the illuminating light supply unit 30 is connected to the control part 2.

Two electrodes project rearwardly from the light source lamp 32. The electrodes are inserted into the socket 33 and electrically connected to connecting pins which are disposed behind the socket 33. The proximal ends of the connecting pins are secured to respective electrode plates 43a and 43b which are disposed to face each other across an insulating plate 44.

One electrode plate 43a is always in contact with the positive electrode of the battery 100, and the other electrode plate 43b is electrically connected with the inner casing 31a by thread engagement. In this way, various members in this part are secured to the inner casing 31a.

Figure 4:
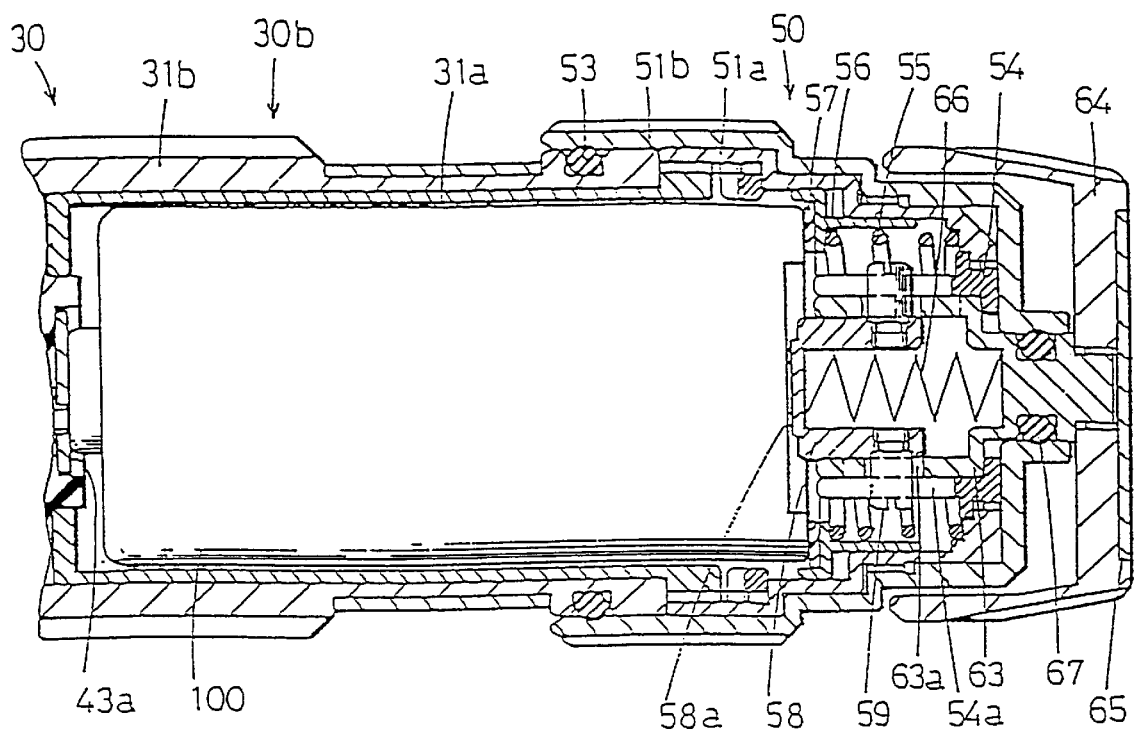
FIG. 4 is a fragmentary sectional view showing a battery chamber portion and a cap, which forms a part of the illuminating light supply unit in the first embodiment of the present invention.

FIG. 4 shows the battery chamber portion 30b. A cap 50 is detachably thread-engaged with the end portion of the cylindrical inner casing 31a, which accommodates the battery 100. The cap 50 incorporates a switch for ON/OFF controlling the supply of electric power from the battery 100 to the light source lamp 32.

An outer cylinder 51b, which is made of a material of good corrosion resistance, forms the outer wall of the cap 50. An inner cylinder 51a, which is made of a metal of good electrical conductivity, is disposed inside the outer cylinder 51b in contact with the inner peripheral surface of the outer cylinder 51b. The inner cylinder 51a is detachably thread-engaged with the inner casing 31a. The outer cylinder 51b and the inner cylinder 51a are integrated together by thread engagement and bonding.

Further, a sealing O-ring 53 is disposed in the area of fit between the outer peripheral surface of the battery chamber-side end portion of the outer casing 31b and the inner peripheral surface of the outer cylinder 51b of the cap 50, thereby preventing water from entering the inside of the cap 50 through the area of fit therebetween.

A cap body 54, which is made of a metal of good electrical conductivity, is integrally connected to the other end portion of the inner cylinder 51a of the cap 50 at the inner side of the outer cylinder 51b by thread engagement and bonding.

A first helical compression spring 55 is retained at one end thereof by the inner cylinder 51a to bias the battery 100 toward the lamp chamber portion 30a through a push ring 56 which is axially movably fitted in the inner cylinder 51a, thereby ensuring the contact between the positive electrode of the battery 100 and the electrode plate 43a.

The first helical compression spring 55 is disposed in coaxial relation to the battery 100, and the push ring 56 abuts on the peripheral edge of the battery 100 so as not to contact the negative electrode of the battery 100. Reference numeral 57 denotes a ring-shaped washer of good slip properties.

A rotating cam cylinder 63 is fitted in the cap body 54 so as to be rotatable about the axis of the cap 50. A switch control ring 64 is integrally connected to the head of the rotating cam cylinder 63, which projects at the projecting end of the cap 50, by thread engagement and bonding.

The switch control ring 64 has a substantially bowl-like configuration, and is disposed so as to surround the end portion of the cap 50. Reference numeral 65 denotes a decorative plate.

The head portion of the rotating cam cylinder 63 is rotatably fitted to the inner peripheral surface of the end portion of the outer cylinder 51b, and an O-ring 67 is fitted in the area of fit between the rotating cam cylinder 63 and the outer cylinder 51b. Thus, the illuminating light supply unit 30 is formed into a watertight structure which prevents water from externally entering the illuminating light supply unit 30 through any portion thereof.

A movable contact member 58 contacts the negative electrode of the battery 100. The movable contact member 58 is formed in the shape of a cylinder, one end of which is closed, from a rigid metallic material of good electrical conductivity. The movable contact member 58 is fitted in the rotating cam cylinder 63 so as to be able to axially project from and withdraw into the rotating cam cylinder 63.

The movable contact member 58 has a contact 58a which is formed on the bottom of the movable contact member 58.

The movable contact member 58 is biased by a second helical compression spring 66 to press the contact 58a against the central portion of the negative electrode of the battery 100. The helical compression spring 66 is made, for example, of a copper alloy such as phosphor bronze or beryllium copper.

Figure 5:
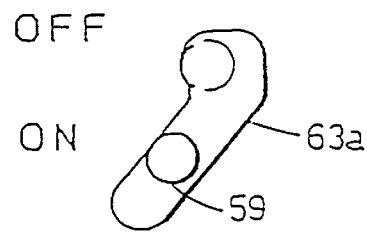
FIG. 5 is a development of a cam groove in the first embodiment of the present invention.

A pair of guide pins 59 project from the outer peripheral surface of the movable contact member 58. The guide pins 59 are made of a material of good electrical conductivity. Each guide pin 59 extends through a cam groove 63a formed in the rotating cam cylinder 63 and is engaged with an axial slot 54a formed in the cap body 54. FIG. 5 shows the configuration of the cam groove 63a.

Accordingly, the engagement between the guide pins 59 and the slots 54a prevents the movable contact member 58 from rotating about the axis, but enables, when the switch control ring 64 is rotated, the rotating cam cylinder 63 to rotate about the axis together with the switch control ring 64, causing the guide pins 59, which are integral with the movable contact member 58, to move axially by the action of the cam grooves 63a. Thus, turning the switch control ring 64 enables the switch to change over between an ON state where the movable contact member 58 is in contact with the negative electrode of the battery 100 and an OFF state where the movable contact member 58 is out of contact with the negative electrode of the battery 100.

In the ON state, the negative electrode of the battery 100 is electrically connected to the negative electrode plate 43b through metallic members of good electrical conductivity which are sealed in the illuminating light supply unit 30 so as to be isolated from the outside, and which are in contact with each other, such as the movable contact member 58, the second helical compression spring 66, the rotating cam cylinder 63, the cap body 54, and the inner casing 31a.

According to the present invention, a heat-insulating cover, which is made of a material of low thermal conductivity, covers the outer surface of an armoring member disposed at a position where it is heated by heat radiated from a light source lamp of an illuminating light supply unit attached to the endoscope control part. Therefore, there is no likelihood of the operator's hand touching a heated portion of the endoscope, which would hinder an endoscopic operation. Accordingly, the operator can perform an endoscopy without anxiety.

Figure 6:
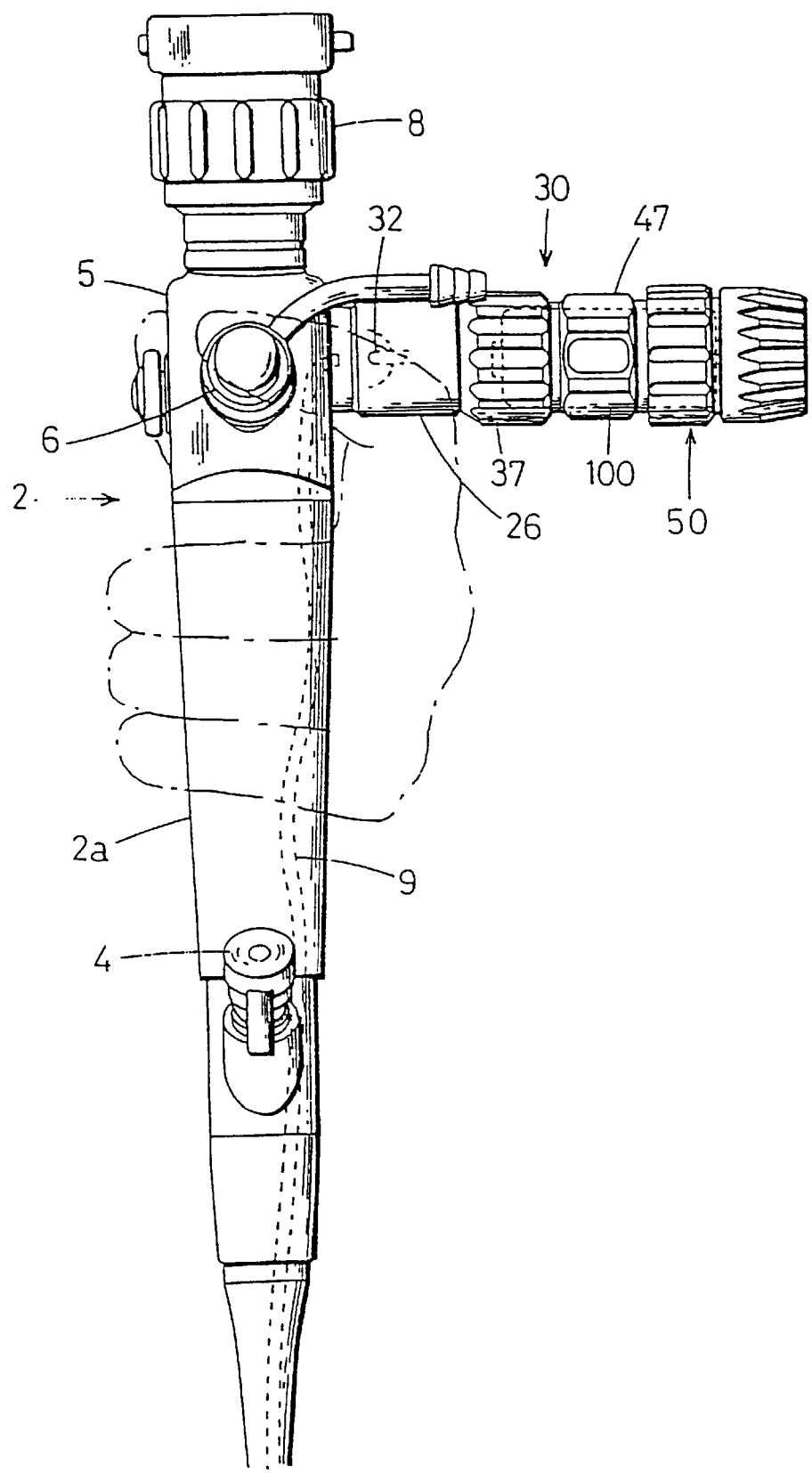
FIG. 6 is a front view of a portable endoscope according to a second embodiment of the present invention.

FIGS. 6 to 9 show a second embodiment of the present invention. FIG. 6 is a front view of a portable endoscope according to the second embodiment, particularly showing a control part thereof. From the viewpoint of the external appearance, the second embodiment differs from the above-described first embodiment only in that a grip portion 47 is provided on an intermediate portion of the illuminating light supply unit 30. In this embodiment, a rotatable fastening ring 37 is used.

In the second embodiment, members or portions which are the same as those in the first embodiment are denoted by the same reference numerals as those in the first embodiment, and description thereof will be given only briefly or omitted.

Figure 7:
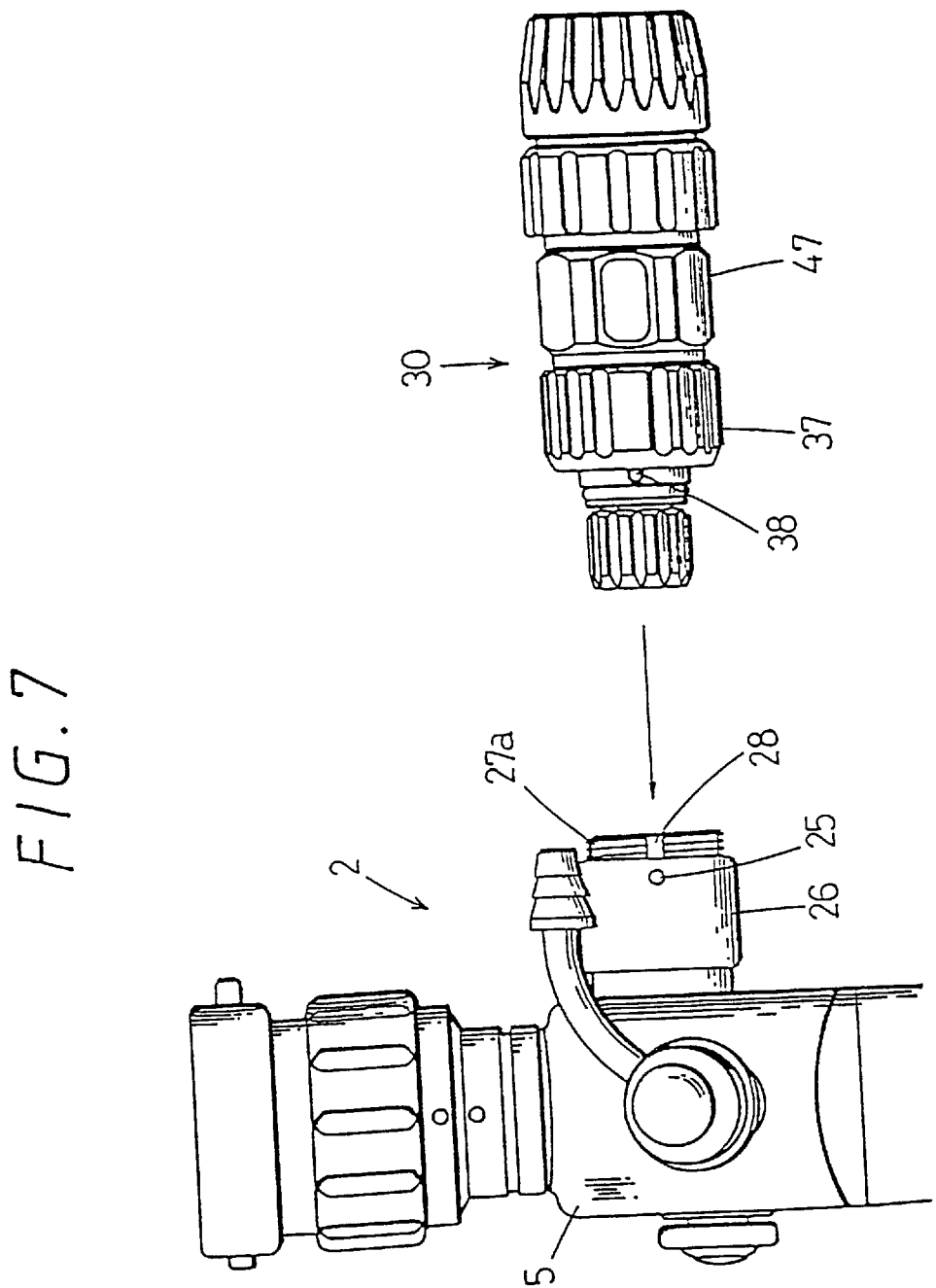
FIG. 7 is a fragmentary front view of the second embodiment of the present invention in a state where an illuminating light supply unit is detached from an endoscope control part.

FIG. 7 shows a state where the illuminating light supply unit 30 is detached from the control part 2. A unit connecting socket 27 projects from the control part 2, as described later. The unit connecting socket 27 has an external thread 27a formed on a projecting end portion thereof. A cylindrical cover 26 is made of a plastic material.

The illuminating light supply unit 30 is provided with a fastening ring 37. The fastening ring 37 has an internal thread for engagement with the external thread 27a of the unit connecting socket 27, which is provided on the control part 2. The fastening ring 37 is adapted to be rotatable about the axis.

The illuminating light supply unit 30 has a positioning pin 38 which is fittable into a regulating groove 28 formed in the projecting end portion of the unit connecting socket 27. When the illuminating light supply unit 30 is to be connected to the control part 2, the positioning pin 38 is fitted into the regulating groove 28 to regulate the orientation of the illuminating light supply unit 30 with respect to the control part 2. A positioning index mark 25 is provided on the cylindrical cover 26.

Figure 8:
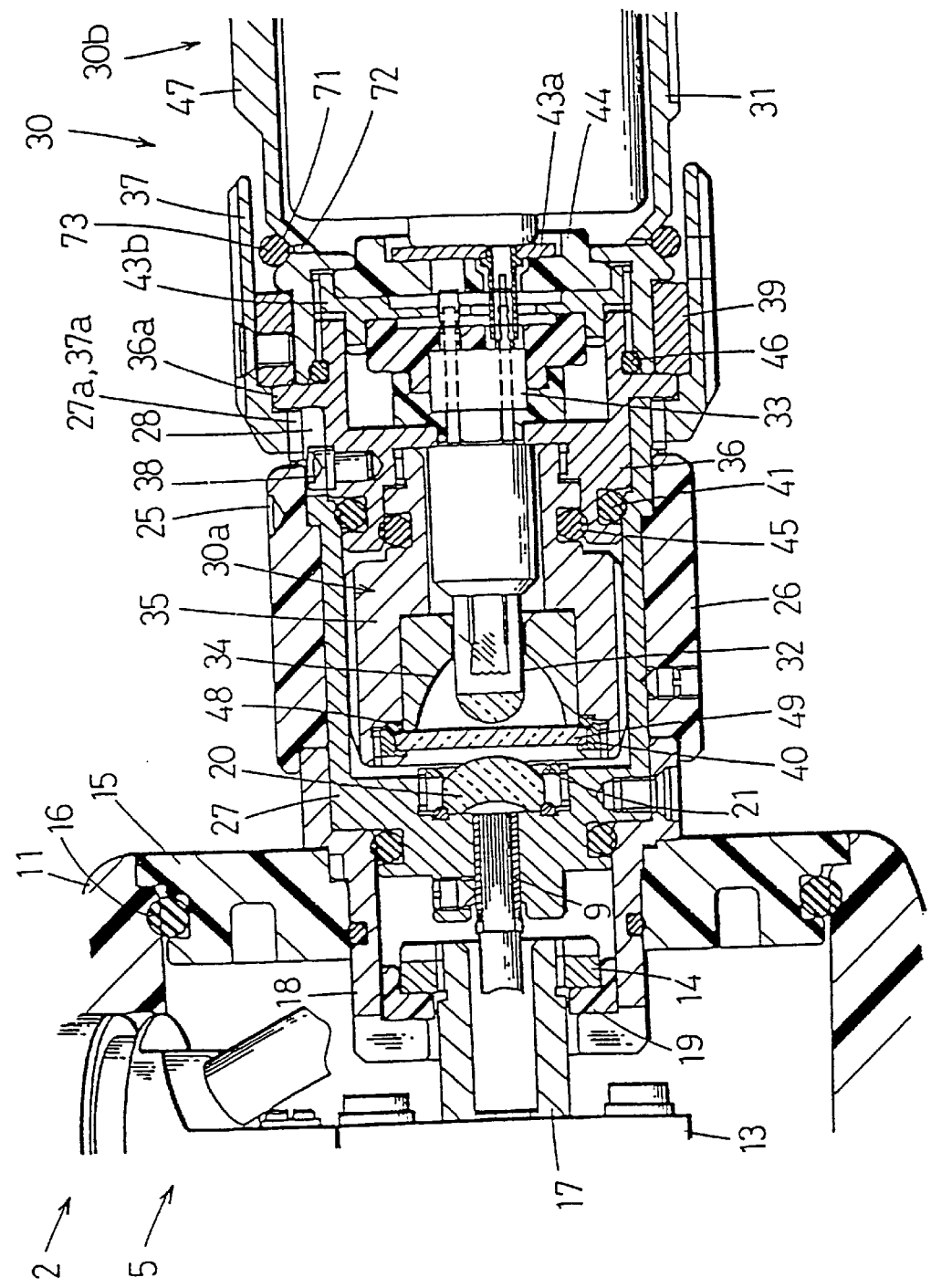
FIG. 8 is a fragmentary sectional view of the second embodiment of the present invention, showing a joint between the endoscope control part and the illuminating light supply unit.

FIG. 8 shows the joint between the control part 2 and the illuminating light supply unit 30. In this embodiment, an O-ring 48 is fitted to the outer edge portion of the inner side of the cover glass 49 to effect hermetic sealing so that water or other fluid cannot externally enter the lamp chamber casing 35.

A connecting cylinder 36 is secured to both the lamp chamber casing 35 and a battery chamber casing 31 by thread engagement to connect the two casings 35 and 31. An O-ring 45 hermetically seals the area of fit between the lamp chamber casing 35 and the connecting cylinder 36. An O-ring 46 hermetically seals the area of fit between the battery chamber casing 31 and the connecting cylinder 36. It should be noted that the distal end portion of the connecting cylinder 36 is fitted into the unit connecting socket 27.

The fastening ring 37 has a distal end portion which is slightly smaller in diameter than the other portion of the ring 37. The smaller-diameter portion of the fastening ring 37 is provided with an internal thread 37a which is engageable with the external thread 27a of the unit connecting socket 27.

An annular member 39 is screwed to the inner peripheral surface of an intermediate portion of the fastening ring 37. The annular member 39 is rotatably fitted on the outer peripheral surface of the battery chamber casing 31. A collar 36a projecting from the connecting cylinder 36 is loosely held between the annular member 39 and the internal thread 37a.

Accordingly, the fastening ring 37 is almost immovable in the axial direction but is rotatable about the axis. Thus, rotation of the fastening ring 37 enables the internal thread 37a on the distal end portion of the ring 37 to be engaged with or disengaged from the external thread 27a of the unit connecting socket 27.

When the lamp chamber casing 35 at the distal end of the illuminating light supply unit 30 is to be inserted into the unit connecting socket 27 projecting from the control part 2, the illuminating light supply unit 30 is first aligned with respect to the control part 2 by rotating it such that the positioning pin 38 is fitted into the regulating groove 28. At this time, it is preferable to hold the grip portion 47, which is formed as a somewhat thick portion on the outer peripheral surface of the battery chamber casing 31.

Upon completion of the alignment in the rotational direction, the fastening ring 37 is rotated to engage its internal thread 37a with the external thread 27a on the projecting end of the unit connecting socket 27, and properly tightened. Thus, the illuminating light supply unit 30 is connected to the control part 2. In this state, the distal end portion of the connecting cylinder 36 is fitted in the unit connecting socket 27, and the fitting surface of the connecting cylinder 36 is hermetically sealed by the O-ring 41. The illuminating light supply unit 30 can be detached from the control part 2, as shown in FIG. 7, by disengaging the fastening ring 37 from the unit connecting socket 27.

Figure 9:
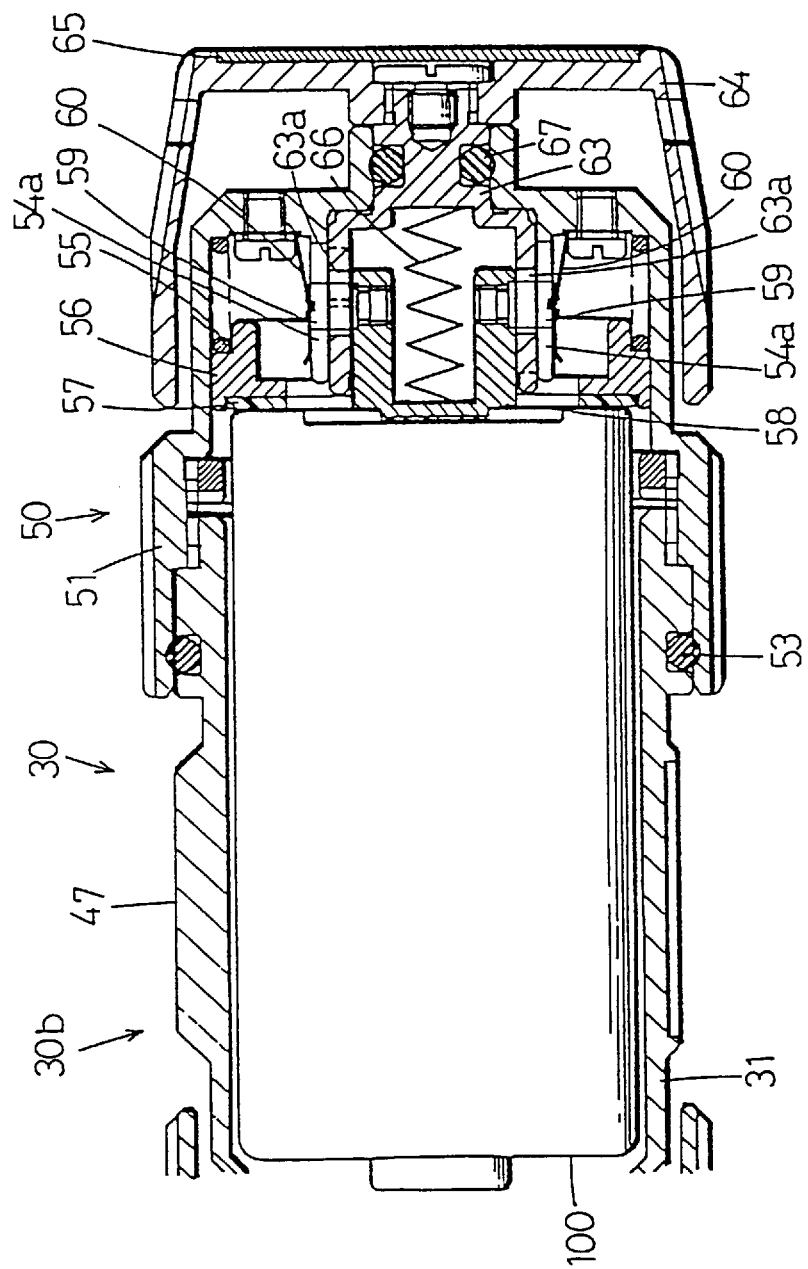
FIG. 9 is a fragmentary sectional view showing a battery chamber portion and a cap, which forms a part of the illuminating light supply unit in the second embodiment of the present invention.

FIG. 9 shows the battery chamber portion 30b. The battery chamber casing 31 and a cap body 51 each have a metallic single-wall structure. Leaf springs 60 are provided in contact with the respective head portions of the guide pins 59 to ensure electrical connection between the battery chamber casing 31 and the cap body 51.

Accordingly, in a switch-ON state, the negative electrode of the battery 100 is electrically connected to the negative electrode plate 43b through the movable contact member 58, the guide pins 59, the leaf springs 60, the cap body 51, the battery chamber casing 31, etc.

The structure of the battery chamber portion 30b in the second embodiment is the same as that in the first embodiment except for the above-described point. The illuminating light supply unit 30 is formed into a hermetic structure as a whole.

However, as shown in FIG. 8, a V-groove 71 having a V-shaped cross-sectional configuration is formed on the forward end of the battery chamber casing 31, which forms an outer wall of the battery chamber portion 30b, such that the V-groove 71 extends over the entire circumference of the outer surface of the battery chamber casing 31. The battery chamber casing 31 is provided with a plurality of circumferentially spaced communicating holes 72 to provide communication between the bottom of the V-groove 71 and the inside of the battery chamber portion 30b.

An O-ring 73, which is made of an elastic and stretchable rubber material, is externally fitted into the V-groove 71. The diameter of the O-ring 73 is smaller than that of the V-groove 71. Therefore, the O-ring 73 is fitted in close contact with the slanted walls of the V-groove 71 in such a manner as to fasten the V-groove 71 tightly.

Accordingly, the close contact surface of the O-ring 73 completely prevents water or other fluid from externally entering the battery chamber casing 31. However, when the gas pressure in the battery chamber portion 30b rises above a predetermined level, the high-pressure gas in the battery chamber portion 30b is released to the outside by passing through the communicating holes 72 and stretching out the O-ring 73 from the inside. When the gas pressure in the battery chamber portion 30b drops below a predetermined level, the O-ring 73 is restored to its normal position for fastening the V-groove 71 tightly.

Thus, the combination of the V-groove 71, the communicating holes 72 and the O-ring 73 forms a relief valve for releasing the pressure in the battery chamber portion 30b to the outside when the pressure rises above a predetermined level. Accordingly, even if a gas is generated from the battery 100 accommodated in the battery chamber portion 30b, the pressure in the battery chamber portion 30b will not rise above a predetermined level.

It should be noted that the present invention is not necessarily limited to the above-described embodiment. For example, the relief valve may be formed by an arrangement other than the combination of the V-groove 71 and the O-ring 73. The present invention may also be applied to a light source apparatus for an endoscope other than a portable endoscope.

According to the present invention, the light source apparatus is provided with a relief valve for releasing the pressure in the battery accommodating chamber to the outside when the pressure rises above a predetermined level. Therefore, even if a gas is generated from a battery accommodated in the hermetically sealed light source apparatus, the pressure in the light source apparatus will not rise abnormally. Accordingly, the light source apparatus is free from such problems as a rapture of the outer wall of the apparatus, and blow-off of the cap.

A reliable relief valve can be constructed at low cost without taking up space by providing communicating holes in the bottom of a groove which is formed to extend over the entire circumference of the outer surface of a member forming the outer wall of the battery chamber portion, and externally fitting a ring-shaped elastic sealing member into the groove.

While the invention has been described by reference to specific embodiments chosen for purposes of illustration, it should be apparent that numerous modifications could be made thereto by those skilled in the art without departing from the basic concept and scope of the invention.

We claim:

1. A portable endoscope having a control part and an illuminating light supply unit, in which the control part has an entrance end portion of a light guide that transmits light to illuminate an object, the illuminating light supply unit containing a light source lamp that supplies illuminating light to the light guide, the illuminating light supply unit being connected to the control part said portable endoscope comprising:

an armoring member disposed at a position where it is heated by heat radiated from a light source lamp of said portable endoscope; and a heat-insulating cover that covers an outer surface of said armoring member, said heat-insulating cover being made of a material having a low thermal conductivity, an illuminating light supply unit of said portable endoscope being detachable with respect to a control part of said portable endoscope, wherein said armoring member comprises a cylindrical member that projects from said control part to connect said illuminating light supply unit to said control part.

2. A portable endoscope according to claim 1, wherein said heat-insulating cover has a cylindrical configuration for covering an outer surface of said armoring member.

3. A portable endoscope having a control part and an illuminating light supply unit, in which the control part has an entrance end portion of a light guide that transmits light to illuminate an object, the illuminating light supply unit containing a light source lamp that supplies illuminating light to the light guide, the illuminating light supply unit being connected to the control part, said portable endoscope comprising:

an armoring member disposed at a position where it is heated by heat radiated from a light source lamp of said portable endoscope; and a heat-insulating cover that covers an outer surface of said armoring member, said heat-insulating cover being made of a material having a low thermal conductivity, an illuminating light supply unit of said portable endoscope being detachable with respect to a control part of said portable endoscope, wherein said armoring member transfers heat to a metallic member which forms an outer wall of said illuminating light supply unit.

* * * * *

UNITED STATES PATENT AND TRADEMARK OFFICE
CERTIFICATE OF CORRECTION

PATENT NO. : 5,865,727
DATED : February 2, 1999
INVENTOR(S) : Hiroshi SANO et al.

It is certified that error appears in the above-identified patent and that said Letters Patent is hereby corrected as shown below:

On the title page, item [30]:
Foreign Application Priority Data,
line 3, change "Mar. 9, 1996" to ---Mar. 7, 1996 ---.

At column 10, line 28 (claim 1, line 7) of the printed patent, change "part" to ---part,---.

Signed and Sealed this

Sixth Day of July, 1999

Q. TODD DICKINSON

*Attest:*

*Attesting Officer*   Acting Commissioner of Patents and Trademarks